United States Patent [19]

Kozulic

[11] Patent Number: 5,458,760
[45] Date of Patent: Oct. 17, 1995

[54] GEL COMPOSITION IN GELS FOR SUBMURGED GEL ELECTROPHORESIS

[75] Inventor: Branko Kozulic, Zurich, Switzerland

[73] Assignee: Elchrom Ltd., Horgen, Switzerland

[21] Appl. No.: 941,107

[22] PCT Filed: Feb. 21, 1992

[86] PCT No.: PCT/EP92/00368

§ 371 Date: Dec. 24, 1992

§ 102(e) Date: Dec. 24, 1992

[87] PCT Pub. No.: WO92/15868

PCT Pub. Date: Sep. 17, 1992

[30] Foreign Application Priority Data

Mar. 1, 1991 [GB] United Kingdom .................... 9104411

[51] Int. Cl.$^6$ ....................................................... C25B 9/00
[52] U.S. Cl. ................................. 204/299 R; 204/182.8; 252/315.1
[58] Field of Search ............................ 204/299 R, 182.8; 252/315.1

[56] References Cited

U.S. PATENT DOCUMENTS

| | | | |
|---|---|---|---|
| 4,650,556 | 3/1987 | Hashiue et al. | 204/182.7 |
| 4,834,854 | 5/1989 | Sugihara et al. | 204/182.8 |
| 4,857,163 | 8/1989 | Gurske et al. | 204/299 R |
| 4,963,243 | 10/1990 | Ogawa et al. | 204/299 R |

OTHER PUBLICATIONS

Patent Abstracts of Japan, vol. 10, No. 334 (P–515) (2390), Nov. 13, 1986, & JP–A–61 139 752, Jun. 27, 1986.
Patent Abstracts of Japan, vol. 11, No. 19 (P–537) (2466), Jan. 20, 1987, & JP–A–61 194 342, Aug. 28, 1986.

*Primary Examiner*—John Niebling
*Assistant Examiner*—C. Delacroix-Muirhcid
*Attorney, Agent, or Firm*—Nikaido, Marmelstein, Murray & Oram

[57] ABSTRACT

The method of electrophoresis uses for separation of charged species their different mobilities in an electric field. The process is usually carried out by forcing the molecules to migrate through an aqueous gel. The gels are run in essentially two types of electrophoretic units: vertical and horizontal ones. It was found that in the standard submerged electrophoresis units the resolution of DNA in the poly(NAT) gels was never so good as in the vertical system. It was observed that by looking at the gel from above under an angle declined from the vertical, the viewed DNA bands in the gel were much sharper than they were pictured on the photograph taken by a camera positioned more or less vertically above the gel. On basis of this observation it was assumed that the diffuseness of bands seen on the photograph did not originate from a real diffuseness of bands in the gel, but rather from the vertical position of the camera and bending of the bands against the vertical axis. If the bands in the gel could be made essentially vertical, then the resolution taken by the usually positioned camera would be qualitatively better and besides that independent of the sample volume. It is the main goal to prevent such bending of bands in gels during electrophoresis.

32 Claims, 4 Drawing Sheets

5,458,760

GEL COMPOSITION IN GELS FOR SUBMURGED GEL ELECTROPHORESIS

BACKGROUND OF THE INVENTION

Electrophoresis is a well known process for separation of charged species which utilizes different mobilities of these species in an electric field. The mobilities depend on the electrophoresis medium, electric field strength and characteristics of ions themselves, including net surface charge, size and shape. Small species, like metal ions, as well as large species such as viruses have been separated by electrophoretic techniques, but electrophoresis is currently used mostly for separation of biological macromolecules, including proteins, nucleic acids and their derivatives. The process is usually carried out by forcing the molecules to migrate through an aqueous gel. The gels used in electrophoresis are composed of natural or synthetic polymers. Agarose is the most widely used natural material and polyacrylamide gels represent the most common synthetic matrix. The gels are run in essentially two types of electrophoretic units: vertical and horizontal ones. In horizontal units the contact between the electrodes and the gel may be established directly or by means of wicks. Alternatively, in submerged gel electrophoresis the gel is immersed in buffer which serves as a conductive medium between electrodes and the gel. This format is the simplest and is widely used for analysis of nucleic acids. Agarose gels are almost exclusively used for submerged gel electrophoresis of nucleic acids. A new synthetic matrix has been introduced for analysis of proteins and nucleic acids by Kozulic et al (U.S. patent application Ser. No. 328,123, Analytical Biochemistry 163 (1987) 506–512 and Analytical Biochemistry 170 (1988) 478–484). It is based on an acrylic monomer, N-acryloyl,tris(hydroxymethyl)aminomethane (NAT). The poly(NAT) gels were found to be more porous than polyacrylamide gels but less porous than agarose gels. Therefore they offered advantages for separation of large proteins and those nucleic acids whose size is out of the optimal separation range of agarose and polyacrylamide gels. In the cited references, the superior properties of the poly(NAT) gels for analysis of DNA were demonstrated after running the gels in a vertical format. However, it was found that in the standard submerged electrophoresis units the resolution of DNA in the poly(NAT) gels was never so good as in the vertical system. The major difference was observed in the lower half of the gel, where the bands became much more diffuse. Moreover, the DNA fragments in the middle lanes migrated further than the corresponding fragments in the outer lanes. This phenomenon is known as the smiling effect. Further, very often DNA bands were straight only in the middle but the edges were bent upwards. The occurrences described above were eliminated when the gels were run in an improved apparatus for submerged gel electrophoresis (Kozulic and Heimgartner, UK Patent Application 9024428.6). In that apparatus buffer cooling and recirculation control the heat produced during electrophoresis and prevent buffer ion depletion in the electrode compartment. In addition, the electric field is more homogenous than in the standard submerged electrophoresis units. The combination of these three improvements has resulted in better resolution of DNA fragments in poly(NAT) gels.

The poly(NAT) gels run in the improved apparatus were usually three millimeters thick. The sample wells were formed with combs 2.5 mm deep, 1.5 mm wide and 5.5 mm long. Thus volume of the sample well should be about 20 µl, but in practice it is about 15 µl because the wells distort slightly after removal of the comb. When the sample volume was from 2 to 5 µl, the resolution of DNA fragments was excellent but it was rather poor, as revealed by a photograph of the gel, when the sample volume was 10 µl or more. That remit was in accordance with many reports in prior art showing that a small sample volume was essential for optimal resolution. Therefore, the poor resolution in submerged poly(NAT) gels at higher sample volumes was initially regarded as normal. Ethidium bromide was used to stain DNA in poly(NAT) gels and the fluorescence of DNA-ethidium bromide complexes was visualized under a UV light. It was by casualty observed that by looking at the gel from above under an angle declined from the vertical, the viewed DNA bands in the gel were much sharper than they were pictured on the photograph taken by a camera positioned more or less vertically above the gel. On basis of this observation it was assumed that the diffuseness of bands seen on the photograph did not originate from a real diffuseness of bands in the gel, but rather from the vertical position of the camera and bending of the bands against the vertical axis. As a consequence of this observation the following object of an invention has crystallized out: If the bands in the gel could be made essentially vertical, then the resolution taken by the usually positioned camera would be qualitatively better and besides that independent of the sample volume. It is now the main goal of the following discussion to describe factors causing bending of bands in gels during electrophoresis and practical means to greatly diminish such bending.

OBJECTIVES OF THE INVENTION

It is an objective of the present invention to find out the causes of the bending of bands in gels run by submerged gel electrophoresis and demonstrate how to prevent it.

It is another objective of the present invention to provide practical means to greatly diminish such bending.

DETAILED DESCRIPTION OF THE INVENTION

The invention will be illustrated with reference to 15 figures and 16 examples which include more detailed descriptions of the figures. Each figure represents a schematic side view of the electrode compartment and a gel section with DNA bands. Electrodes are depicted as one or two dots with anode always on the right. The level of buffer above the gel is indicated as a dashed line. The gel support is not shown.

Figure 1A:
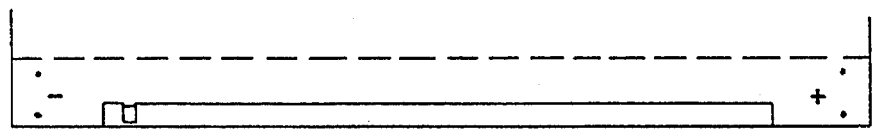
FIG. 1a is a schematic side view of a gel in an electrode compartment, with a sample placed in a sample well at the left side of the gel. The two dots close to each side of the compartment represent electrodes and buffer level is indicated by a dashed line.
Figure 1B:
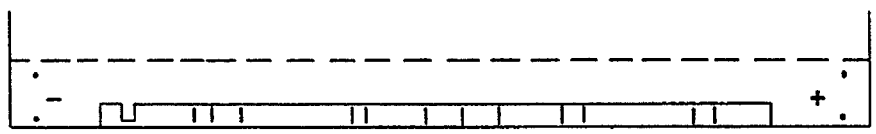
FIG. 1b is a schematic side view of a gel with hypothetical, perfectly vertical bands representing zones of separated molecules.

In submerged gel electrophoresis, a gel is placed on a platform and covered with a buffer which serves as an electrically conductive medium. A sample is applied in the sample well (FIG. 1a) and charged species from the sample separate as they migrate in the electric field. As shown in FIG. 1b, at the end of the run the separated bands should be vertical because the starting zone was vertical. However, after cutting a gel strip and placing it on its side under UV light it was observed (FIG. 2) that the separated bands were always bent in poly(NAT) gels.

There are five major factors which could generate this effect. They include inhomogeneous electric field, electroendosmosis, nonuniform heat dissipation, different gel strength and different conductivity in the gel and electrophoresis buffer. Any combination of these factors is also possible and the contribution of each of them to the effect may be of different magnitude.

Electric field inhomogeneity was considered as the first possible cause of the bands bending. In the standard submerged electrophoresis apparati the electric field lines are curved in the gel compartment because the electrodes are situated below the gel compartment. In the improved apparatus (Kozulic and Heimgartner, UK Application 9024428.6) the homogeneity of electric field is better since the field is created by electrodes positioned essentially in the same plane to gel. However, the bending of DNA bands was noticed in the gels run in standard units as well as in the improved unit equipped with one or two platinum wires for anode and cathode. As indicated before (Kozulic and Heimgartner, UK Application 9024428.6), the electric field created by electrodes comprising two wires vertically distant from each other about 2–20 mm is substantially more homogenous than the field created by only one wire. Poly(NAT) gels were run after placing them in the middle between the pair of electrodes at several distances (5, 10 and 35 mm), or closer to the anode or cathode. In addition, the vertical distance of platinum wires was varied from 3 to 10 min. In all gels the general bending pattern shown in FIG. 2 persisted, although there were differences in the extent of bending especially of bands representing DNA fragments below 1 kbp. From these experiments it was concluded that improvement in electric field homogeneity alone was not sufficient to overcome the bending of DNA bands.

Figure 2:
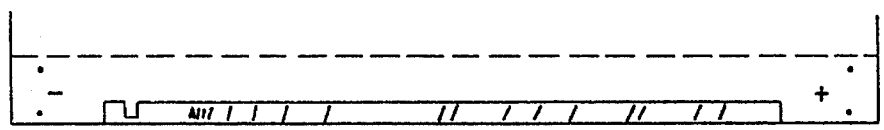
FIG. 2 is a schematic side view of a 6% poly(NAT) gel with separated DNA bands, as described in Example 1.

During electrophoresis there is friction caused by movement of ions in the electrophoresis medium which results in production of heat, known as Joule heat. The heat is produced in the gel and in the buffer surrounding it. Since the gel gives more resistance to migration of ions, more heat is produced in the gel. That heat is dissipated into the buffer and the platform on which the gel rests. It is reasonable to assume that the heat is more efficiently transferred to the circulating buffer than to the platform. The plastic support fixed to the gel bottom additionally reduces the efficiency of heat transfer to the platform. Therefore, if there is a gradient of temperature in the gel, the temperature should be higher close to the bottom. It is known that mobility of an ion in electric field increases with temperature of the medium. Accordingly, a DNA band would migrate further close to the bottom of the gel. However, as shown in FIG. 2 DNA bands migrate further near the surface. A temperature gradient in the gel is therefore excluded as a major reason for banding of DNA bands in a 3 mm thick poly(NAT) gel. This conclusion is supported also by the finding that a similar bending pattern existed in the gels run in the standard unit and in the improved unit. The improved apparatus features buffer circulation and cooling. The platform on which the gel rests is also cooled. Thus it was found that buffer temperature was constant (25° C.°) in this unit but it increased from 22 C.° to 34 C.° in the standard unit after running the gel at 7 V/cm for about 2 hours.

Figure 3:
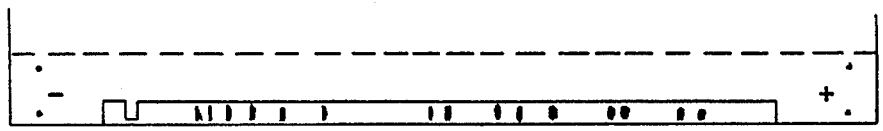
FIG. 3 is a schematic side view of a 6% poly(NAT) gel with separated DNA bands, as described in Example 2.

For convenient handling the poly(NAT) gels were polymerized onto a plastic support described in U.S. Pat. No. 4,415,428. During polymerization covalent bonds are formed between the vinyl groups of the support and the polymer chains comprising the gel. It is expected therefore that the gel is stronger near the plastic support at the bottom and if there is a gradient of gel strength, DNA molecules would migrate faster close to the surface. That is indeed the case, as shown in FIG. 2. However, it is difficult to explain the bending pattern by a gradient of gel strength from the bottom to top because some bands are bent more and some less. Since the gel was polymerized in a vertical position with sample wells on the top there was a possibility that a strength gradient extended also along the gel length. However, gels polymerized horizontally, with the support positioned up or down, showed the same banding pattern. To further elucidate the influence of gel strength, a sheet of plastic support was fixed during polymerization on each side of a 6% poly(NAT) gel. If there is a gradient of gel strength, the gel should be weaker in the center and DNA molecules should migrate faster in the middle of the gel. FIG. 3 shows that this is not the case. The bands are vertical and hence it was concluded that the bending of the bands is not caused by differences in gel strength. Although in this way the bending is eliminated, it is noted that the attachment of a plastic support on top of the gel is not a convenient practical solution because it is more difficult to prepare such gels and because it is necessary to remove the support prior to staining of the gel.

Polymerization of the gel between two plastic sheets eliminated also the influence of inhomogeneity of electric field because the field in the gel was restricted by the plastic support. Second, the migration of ions in and out of the gel through its surface was also prevented. Therefore from FIG.

3 it is not possible to say which is the major factor causing the bending of bands in a submerged gel.

The principal difference between submerged gel electrophoresis and other methods is the fact that five sides of the submerged gel are surrounded by buffer. In the gel ions will mostly migrate in direction of electric field through the gel. During electrophoresis anions initially present in the gel are coming out on the anode side of the gel and cations on the cathode side of the gel. They are continuously being replaced by anions and cations from the buffer on the opposite sides. However, in contrast to other methods, in submerged gel electrophoresis some ions probably go out of the gel through its upper surface due to diffusion and nonuniform electric field. It is also likely that ions enter the gel through this surface. This movement of anions and cations in and out of the gel through its surface would affect the ionic composition in the gel. The change will be clearly larger near the surface. It is known that migration distance of an ion, in our case a DNA molecule, can be described by the following formula:

$$d = utE \quad (1)$$

where u is electrophoretic mobility ($cm^2_s-1V^{-1}$), t is time in seconds and E is electric field strength ($Vcm^{-1}$). By substituting:

$$E = \frac{i}{\kappa} \quad (2)$$

where i is current density ($Acm^{-2}$) and $\kappa$ is conductivity ($Scm^{-1}$) in equation (1) one obtains:

$$d = ut\frac{i}{\kappa} \quad (3)$$

From equation (3) it follows that DNA molecules in a band will migrate the same distance only when the ratio of current density and conductivity remains constant in the gel section through which the band moves. If the ratio changes due to differences in the composition or concentration of ions, then DNA molecules will migrate differently in this section of the gel. As shown in FIG. 2 that is experimentally observed, as DNA molecules close to the gel surface migrated a longer distance.

At this point we should examine the ionic composition of a 6% poly(NAT) gel. One gel has a volume of about 17 ml (92×62×3 mm) but the values are given for 1 l. The NAT monomer (58.8 g) and N,N'-methylene-bis-acrylamide (1.2 g) are dissolved in the buffer (pH 8) composed of 30 mM tris(hydroxymethyl)aminomethane (Tris), 15 mM acetic acid and 0.75 mM ethylenediaminetetraacetic acid disodium salt ($Na_2EDTA$) to give one liter of solution. To polymerize the gel, tetramethylethylenediamine (TEMED) and ammonium persulfate are added at the final concentration of 15 mM and 1.65 mM, respectively. Thus the gel contains four cations (Tris, TEMED, sodium and ammonium) and three anions (acetate, EDTA and sulfate as the breakdown product of persulfate, assuming that the reaction is complete). The concentration of Tris is 30 mM (only a part of it is charged), TEMED 15 mM (most of it has one charge and some molecules may carry two positive charges), sodium 1.5 mM and ammonium 3.3 mM. The concentration of acetate is 15 mM, EDTA 0.75 mM and sulfate 3.3 mM. Thus the molecular weights and number of charges among anions and cations vary widely. Therefore their diffusion and migration rates are also different, which is reflected in differences in equivalent conductivities of the anions and cations. As some ions leave and some enter the gel through its sides and likely through its surface, it is apparent that current density and conductivity of the gel change in a complex way. Since a mathematical treatment of this process seemed complicated and of questionable practical importance, experiments were done to simplify the system by reducing the number of ionic species.

Figure 4:
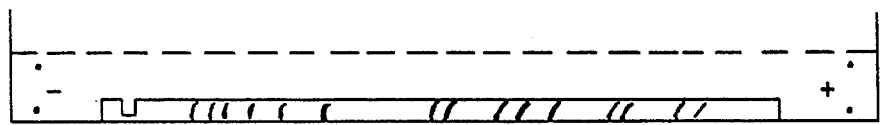
FIG. 4 is a schematic side view of a 6% poly(NAT) gel with separated DNA bands, as described in Example 3.

In the first experiment, sodium was eliminated by using EDTA-free acid in the gel and in the running buffer. The buffer was composed of 30 mM Tris, 11 mM acetic acid and 1.5 mM EDTA. The DNA bands were still bent (FIG. 4). Then both sodium and EDTA were omitted from the buffer and the gel, but the bending persisted.

Figure 5A:
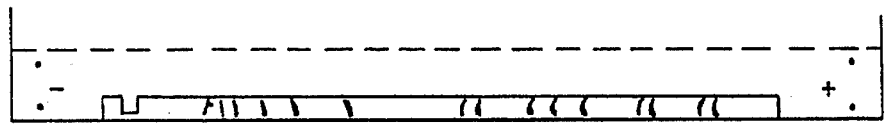
FIG. 5a and 5b represent a schematic side view of a 6% poly(NAT) gel with separated DNA bands, as described in Example 4.
Figure 5B:
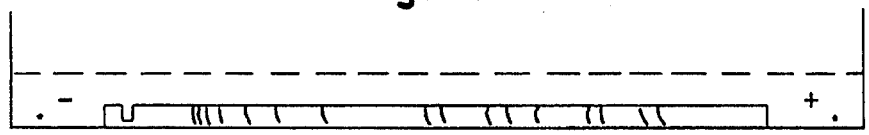

In the gels shown in FIGS. 2–4 the mass to charge ratios of anions and cations were very different. It appeared reasonable to test how a buffer composed of an anion and cation having a similar mass to charge ratio influences the shape of DNA bands. The molar conductivity and diffusion rate of such an anion and cation are expected to be similar. N-methyl glucamine (MW 195) and gluconic acid (MW 196) were chosen. The buffer contained 30 mM N-methyl glucamine and 15 mM gluconic acid. The gel was polymerized in this buffer and electrophoresed in the 30 mM Tris, 11 mM acetate, 1.5 mM EDTA-free acid buffer. As shown in FIG. 5a, the DNA bands were bent but on the other side. That is, DNA molecules close to the plastic support migrated further than the molecules near the surface of the gel, especially in the high molecular weight range. This experiment was a strong indication that ionic composition of the gel has a major impact on the bending of bands. Another gel of identical composition was run in the same buffer but in the electric field created by one platinum wire for the anode and cathode. FIG. 5b shows the same general bending although the shape of some bands is slightly different. This result has indicated again that the electric field does contribute to the bending of bands, but that its contribution is smaller than that of ionic composition.

Figure 6:
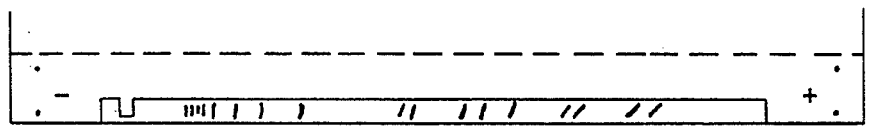
FIG. 6 is a schematic side view of a 6% poly(NAT) gel with separated DNA bands, as described in Example 5.
Figure 7:
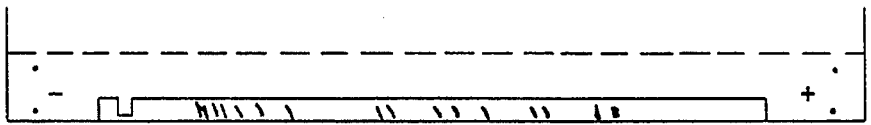
FIG. 7 is a schematic side view of a 6% poly(NAT) gel with separated DNA bands, as described in Example 6.

There was a possibility, however, that the differences in bending were caused by different electroendosmosis in the poly(NAT) gels. It is well known that electroendosmosis influences electrophoretic migration of analyzed molecules (S. Hjerten, Electrophoresis, 1990, 11, 665–690). Electroendosmosis in a gel depends on the concentration and type of charged groups fixed to the matrix. In gels prepared by the free radical polymerization initiated by sulfate radicals there is always a small number of sulfate groups. Further, a sulfate radical, or a hydroxyl radical derived from it, may react with a buffer ion if that ion contains a reactive group. The new radical may be then incorporated into the polymer matrix. It is known that compounds with hydroxyl groups react with free radicals and some buffer ions used here contained three (Tris) or five (N-methyl glucamine and gluconic acid) hydroxyl groups. Incorporation of Tris would make the gel positively charged and it would contain both positive and negative charges if it incorporated N-methyl glucamine and gluconic acid. In order to exclude electroendosmosis due to incorporated buffer ions, poly(NAT) gels were polymerized with TEMED and ammonium persulfate in water and then equilibrated against electrophoresis buffers. One gel was equilibrated against the 30 mM TAE buffer and the other against the 30 mM N-methyl glucamine, 15 mM gluconic acid buffer. The first gel was run in the same TAE and the second in the same N-methyl glucamine-gluconic acid buffer. FIGS. 6 and 7 show that the DNA bands bending in these gels is comparable to the bending in gels which were polymerized in the presence of these buffers. Therefore, it was concluded that electroendosmosis caused by incorporated buffer ions could not have contributed significantly to the bending of bands.

Figure 8:
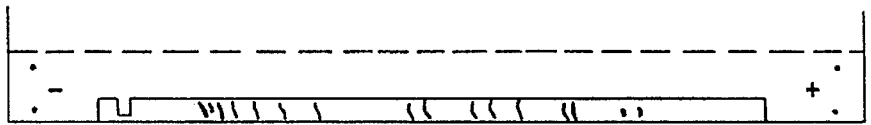
FIG. 8 is a schematic side view of a 6% poly(NAT) gel with separated DNA bands, as described in Example 7.

The other important conclusion from results of FIG. 6 and 7 was that the bending of bands occurred also when the concentration and composition of ions in the gel was identical to that in the buffer. One more experiment was carried out to check this conclusion. Thus, a gel was polymerized in water and advantage was taken of the fact that TEMED is a weak base and that hydrogen sulfate is produced from persulfate. Therefore the solution of TEMED and ammonium persulfate at the concentration used to polymerize the gel has a sufficient buffering capacity to be used as a buffer for electrophoresis. Although the gel and the electrophoresis buffer contained just three ions at the same concentration, the bending of DNA bands was not avoided (FIG. 8).

Figure 9:
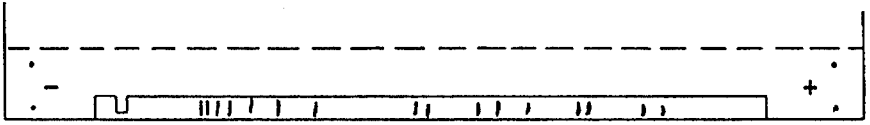
FIG. 9 is a schematic side view of a 6% poly(NAT) gel with separated DNA bands, as described in Example 8.

The above results clearly established two things. First, the ionic composition of the gel and the buffer has a major impact on the bending of bands. Second, bending cannot be avoided by adjusting the composition and concentration of ions in the gel to that in the electrophoresis buffer to the same value. The results also suggested that the nature of ions is important predominantly in relation to its influence on the ratio between current density and conductivity, since similar bending patterns were observed in gels and buffers of different ionic composition. Thus in some gels this ratio is supposedly higher near the surface and in other gels it is higher near the bottom, causing bending in different direction. It seemed reasonable to expect that due to their higher mass to charge ratio, both N-methyl glucamine and gluconic acid have lower electrophoretic mobility than Tris or acetate. Further, since they are larger they also experience more resistance during migration through the 6% poly(NAT) gel. One can assume that during electrophoresis in this buffer the conductivity decreased proportionally more than current density in the gel, when compared to the values of conductivity and current density in the same buffer outside the gel. On the contrary, with TAE buffer in the gel the conductivity decreased less than current density in relation to those in the free buffer. If these assumptions are correct, then it should be possible to prevent bending of bands by adjusting the initial ratio of current density and conductivity in the gel and in the buffer to such a value that i/κ ratio in the gel remains essentially constant during electrophoresis. Ideally, the initial i/κ ratio of the gel and the electrophoresis buffer should be equal and remain constant during the electrophoretic run, but in practice of submerged gel electrophoresis this requirement is difficult to fulfill because the ionic composition of the gel and buffer changes, as described above. The adjustment of the initial i/κ ratio of the gel to that of the 30 mM TAE buffer was attempted empirically, that is a series of gels was polymerized with the same amount of TEMED and ammonium persulfate but at various dilutions of the TAE buffer. This approach appeared logical also because in the gel containing only TEMED and ammonium persulfate the bands were bent on the other side (FIG. 8), indicating that 30 mM TAE in the gel is causing the change in bending direction. After running the gels, there was a clear improvement of the band pattern at lower concentrations of the TAE buffer. The pattern could be further improved by substituting sodium persulfate for ammonium persulfate. FIG. 9 shows that at the optimal TAE buffer concentration (18 mM) there is very little bending of DNA bands. It is noted that this does not mean that 18 mM TAE buffer in the gel provides the ratio of current density to conductivity equal to that of 30 mM TAE buffer surrounding the gel. The gel contained additional ions (TEMED, sulfate, more sodium) which contributed to the current density and conductivity.

It was of interest to see whether the right buffer concentration in the gel could be determined by measuring the current in the electrode compartment containing only the buffer or the buffer plus the gel. The measurement of current was carried out at various voltages without the gel (Table 1, column 1). Then three gels with the optimal buffer concentration (18 mM) were placed in the compartment and the measurement was repeated. Practically the same values were obtained (second column). Three gels with 30 mM TAE gave higher values (column 3). Accordingly, in this simple way it is possible to check whether resistance of the gel is comparable to that of the buffer. From such measurements, however, it is not possible to say whether the gel has the right ionic composition. Further, the precision of voltage and current readings of the common electrophoresis power supplies is not high. In addition, the gel may occupy anywhere from 10 to 90% of the volume between the electrodes, and the precision of measurement will depend also on the ratio between gel and buffer volume. Finally, during electrophoresis at constant voltage the current usually changes due to electrochemical reactions on electrodes and due to migration of some ions, not originally present in the buffer, out of the gel. From these considerations it is apparent that the optimal ionic gel composition can be tuned better empirically by running the gels with slightly different compositions and analyzing the band pattern as described above.

Figure 10A:
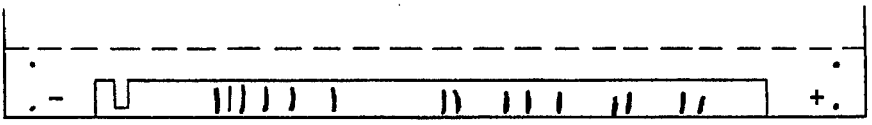
FIG. 10a and 10b represent a schematic side view of 5 mm thick 6% poly(NAT) gel with separated DNA bands, as described in Example 10.

From equation (3) it is apparent that migration distance of a band depends on current per $cm^2$ and conductivity per cm. Therefore it was reasonable to check whether thicker or longer gels may require another ionic composition for optimal band pattern. As can be seen from FIG. 10, that is indeed the case. In the 5 mm thick 6% poly(NAT) gel at 18 mM TAE buffer DNA bands are bent (FIG. 10b), although this concentration is optimal for 3 mm thick gels. The bands are less bent at 30 mM TAE buffer (FIG. 10a).

Figure 11A:
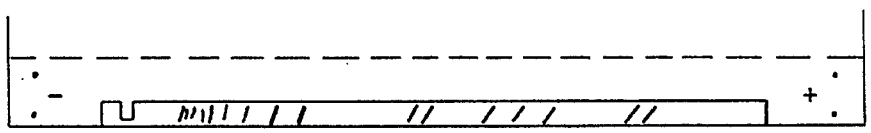
FIG. 11a and 11b represent a schematic side view of a 9% poly(NAT) gel with separated DNA bands, as described in Example 11.
Figure 11B:
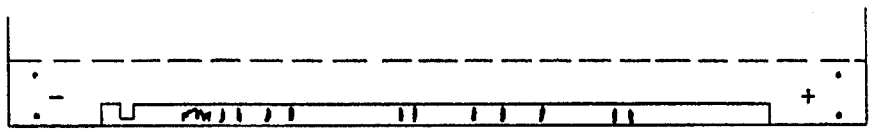

The ionic composition of the gel needs to be adjusted also after changing the gel concentration. Thus, in a 9% poly(NAT) gel at 18 mM buffer the DNA bands are bent (FIG. 11a) but at 50 mM they are almost vertical (FIG. 11b). It is noted that at gel concentrations of 9% and higher the bands tend to become more round and at lower volumes they appear as spots when looked from the side. They also tend to migrate slightly closer to the bottom at the higher buffer concentrations optimal for resolution.

Figure 12A:
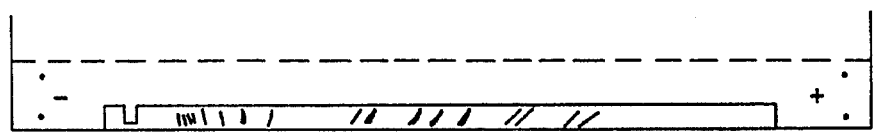
FIG. 12a and 12b represent a schematic side view of a 5% polyacrylamide gel with separated DNA bands, as described in Example 12.
Figure 12B:
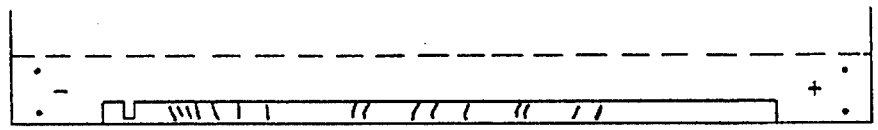
Figure 13A:
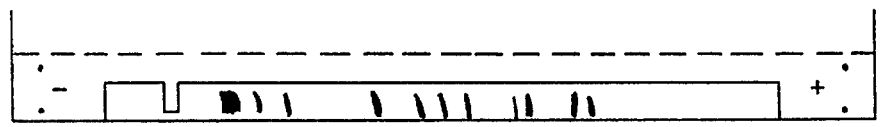
FIG. 13a and 13b represent a schematic side view of a 4% NuSieve gel with separated DNA bands, as described in Example 13.
Figure 13B:
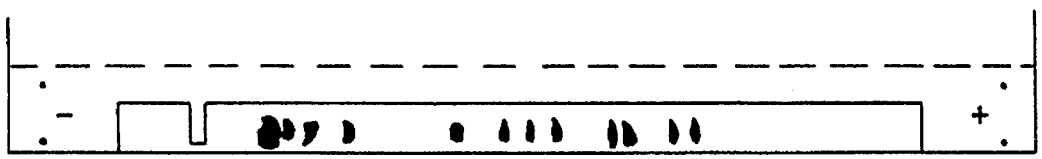

Since all experiments described above were carried out with poly(NAT) gels it was important to determine whether the same phenomenon takes place in other gels used for submerged electrophoresis. As shown in FIG. 12a, the DNA bands are also bent in a 5% polyacrylamide gel containing 20 mM TAE but are less bent at 35 mM buffer (FIG. 12b). Likewise, in 4% hydroxyethylated agarose (U.S. Pat. No. 3,956,273) the DNA bands are bent when the buffer concentration in the gel is equal to that surrounding the gel (FIG. 13a). The shape of bands is better at 45 mM buffer, as shown in FIG. 13b.

In an electrolyte solution, the electrical current is equivalent to the transport of ions. Ions having the same mobility transport current with the same efficiency. The buffers used above were composed of ions with various mobilities and concentrations. It was of interest to determine the part of current transported by anions and the part transported by cations. Further, it was important to see the band pattern in a buffer in which anions and cations transport the same amount of current.

First, the current at 10–120 V was measured in solutions containing ions which were present in the gel and the TAE buffer. The solutions and the values at 80 V are given in Table 2. The increase of current was slightly higher than linear at 100 and 120 V for NaCl, $Na_2SO_4$ and KCl. The currents measured in the solutions were proportional to the equivalent conductivities found in the CRC Handbook of Chemistry and Physics (651th Edition, D-171–172). The current transported by each ion was calculated from the equivalent ionic conductivities extrapolated to infinite dilution, assuming that the ratio of the ionic conductivities of anions and cations was not changed in solutions at the concentrations used in the measurements. Thus it was calculated that under experimental conditions specified in Example 14, 5 mM $Na^+$ transports 35 mA, 5 mM $K^+$ 51 mA, 5 mM $Cl^-$ 53 mA, 5 mM $SO_4^{2-}$ 100 mA, 2 mM EDTA (pH 8) 37 mA, 5 mM acetate 29 mA, 15 mM $Tris^+$ 44 mA and 15 mM TEMED (pH 8) 52 mA. From these values it was calculated that the 30 mM TAE buffer should transport 155 mA at 80 V. The value of 158 mA was measured. Further, it was measured that 18 mM TAE buffer containing 15 mM TEMED and 1.65 mM sodium persulfate displays 199 mA at 80 V. This value is 1.26 times higher than the value of the TAE running buffer. Therefore it indicates that the buffer in a 6% poly(NAT) gel should have 1.26 fold higher conductivity than the running buffer in order to achieve the optimal band pattern. It should be noted that pH of the gel buffer is higher (8.8) due to TEMED and hence mobilities of some ions, in particular Tris and TEMED are different from those in the electrophoresis buffer which has a lower pH.

In the 30 mM TAE buffer, 55 mA are transported by cations and 103 mA by anions. This imbalance can be corrected by adding to TAE buffer a salt in which the cation has a considerably higher equivalent conductivity than the anion. There are many such salts, but potassium acetate was chosen because acetate was already present in the buffer. The desired current of the new buffer in this example was set to 158 mA and of that current 79 mA should be transported by anions and 79 by cations. The exact concentrations were calculated from the equation below.

$$158 = 55x + 103x + 29y + 51y \quad (5)$$

$$79 = 55x + 51y \quad (6)$$

where 55 and 103 denote current transported by cations and anions in the 30 mM TAE buffer, respectively, while 29 denotes current transported by acetate and 51 by potassium in 5 mM KOAc, all in mA.

The equations (5) and (6) can be written in a general form:

$$I_t = xI_{bc} + xI_{ba} + yI_{sc} + yI_{sa} \quad (7)$$

$$\tfrac{1}{2}I_t = xI_{bc} + yI_{sc} \quad (8)$$

where $I_t$ is desired total current, $I_{bc}$ is the current transported by buffer cations, $I_{ba}$ is the current transported by buffer anions, $I_{sc}$ is the current transported by salt cation, $I_{sa}$ is the current transported by salt anion and x and y are dilution factors of the original buffer and salt solutions, respectively. It is noted that the concentrations of original buffer and salt solutions should be close to the final ones, that is x and y should not be much larger or smaller than 1, because it is known that conductivity increases with dilution. When it is desirable to keep the buffer concentration constant then x=1 and $I_t$ and y can be calculated from equations (7) and (8). In the analogous way, y may be kept constant and the other two parameters varied.

From equations (5) and (6) it follows that in a solution containing 14.3 mM TAE and 5.2 mM KOAc current will be equally transported by anions and cations and that its value should be 158 mA. The value of 156 mA was measured. In all solutions having the ratio (in mM) of TAE to KOAc of 2.75:1, the current transported by anions and cations will be equal. It is clear that desired concentrations for other ranges or for different solutions can be calculated in the analogous way.

Figure 14:
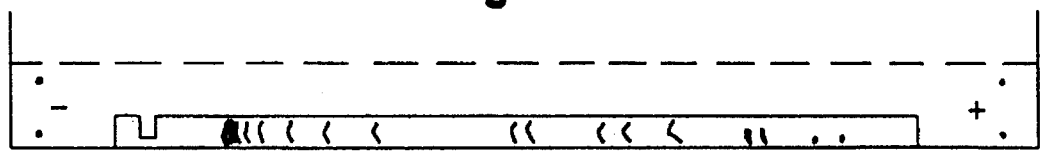
FIG. 14 is a schematic side view of a 6% poly(NAT) gel with separated DNA bands, as described in Example 15.
Figure 15:
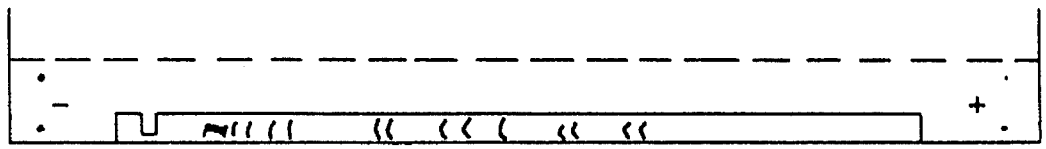
FIG. 15 is a schematic side view of a 9% poly(NAT) gel with separated DNA bands, as described in Example 16.

In a similar manner it was calculated that, at pH 8, the gel buffer should contain 15 mM TEMED, 1.65 mM sodium persulfate, 22.5 mM acetate and 11.6 mM potassium to transport the same current by anions and cations. The current should then be 388 mA and the value of 370 mA was measured. A 6% and a 9% poly(NAT) gel were prepared in the above buffer. The 6% poly(NAT) gel was run in the TAE-KOAc buffer giving 1.26 fold lower current (294 mA was expected and 268 measured in the buffer containing 26.6 mM TAE and 9.7 mM KOAc). The DNA band pattern is shown in FIG. 14. As noted in Example 11, a 9% poly(NAT) gel polymerized in 50 mM TAE buffer gave a good band pattern (FIG. 11). The current at 80 V of 50 mM TAE, 15 mM TEMED and 1.65 mM sodium acetate was 346 mA, that is 2.19 fold higher than in the TAE running buffer (158 mA). The 9% poly(NAT) gel polymerized in the buffer described above was electrophoresed in the TAE-KOAc buffer giving 2.19 lower current than the gel buffer. Thus, the running buffer contained 15.3 mM TAE and 5.6 mM KOAc and the DNA pattern is shown in FIG. 15. It is noted that in both 6 and 9% gel DNA bands are bent and appear as symmetrically bent lines (FIGS. 14 and 15). This result demonstrates that equal transport of current by anions and cations in the running buffer is not sufficient to prevent the bending of bands even if the ratio of the current in the gel and running buffer is adjusted to the same value found optimal for another buffer composition. The band pattern clearly depends also on the ionic composition of the gel and the buffer, in accordance with the results already presented. It is noted that the two gels above did not contain EDTA and Tris, which were present in the running buffer. Further, although the current ratio of the gel and electrophoresis buffers was essentially equal to that measured and found optimal with the TAE buffer, that does not exclude the possibility that this ratio was actually different after formation of the gel. Namely, the sieving of ions by the gel depends on characteristics of each ion. Therefore, two solutions with different ionic compositions giving the same current in water may give different currents in gels of identical polymer composition.

In many experiments described above TAE was employed as the principal buffer. This buffer was initially selected since it is one of the two mostly used buffers for submerged gel DNA electrophoresis (Molecular Cloning, a Laboratory Manual, Eds. Manjarls, T., Fritsch, E. F., and Sambrook, J. Cold Spring Harbor, 1982). Other ionic compositions can obviously be utilized, as shown by numerous examples of this invention. However, to achieve optimal resolution the ionic concentration and composition of the gel and buffer need to be adjusted according to the teaching of this invention. The said adjustment is most conveniently done by preparing a series of gels with slightly different ionic concentration or composition and then examining the band pattern after electrophoresis in a buffer of constant composition and concentration. Alternatively, many gels of the same ionic composition and concentration may be prepared and then each gel run in a buffer of slightly different composition or concentration. Since in one electrophoretic run only one combination can be examined, this approach is time consuming and therefore less preferable. There is one more long way for adjustment of the ionic compositions in the gel and electrophoresis buffer. It requires preparation of a series of gels of the same polymer composition but containing one cation and one anion or one anion and two cations per gel. For instance, one gel may contain 5 mM KOAc, the other 5 mM NaOAc and the third one 5 mM KOAc plus 5 mM NaOAc. From measured conductivity of each gel it is possible to calculate the equivalent conductivity of $Na^+$, $K^+$ and $Ac^-$ in the gel of that particular polymer composition and size. After determination of the equivalent conductivity of each ion present in the gel and in the electrophoretic buffer it is theoretically possible to calculate the ionic compositions and concentrations required to maintain i/κ ratio constant in the gel cross-section through which a band migrates.

It is noted that DNA molecules were used to demonstrate various aspects of the present invention but the improvements disclosed here will be clearly beneficial also in separation of other molecules which migrate as bands in a gel.

The invention will be further illustrated by the following exemplifications, not intended as limitations unless otherwise specifically indicated herein.

Gel preparation, electrophoresis conditions and samples

A 6% poly(NAT) gel, containing 5.88 g of NAT and 0.12 g of Bis in 100 ml of water or a buffer, was polymerized by addition of TEMED (225 μl ) and ammonium persulfate (1,82 ml of a 22 mg/ml solution) into the 100 ml of solution. The dimensions of the gel were 92×62×3 mm. The gels used in experiments described here were left to polymerize at least 16 hours and some were stored in sealed bags at room temperature for no longer that two weeks. No difference in band pattern was observed in the stored gels. The gels were run in the improved submerged electrophoresis apparatus (Kozulic and Heimgartner, UK Application 9024428.6), with one or two platinum wires for the anode and cathode. The two wires were vertically distant 6 mm in most experiments. The gels were run at 7 V/cm, that is 77 V over 11 cm distance. Initial amperage was 140–150 mA. The gels were not pre-electrophoresed since it was noticed that the bending of bands was dependent also on exact duration of pre-electrophoresis.. The Pharmacia constant voltage 200 V/400 mA power supply was used. During electrophoresis, buffer temperature was initially equal to room temperature (17°–21° C.) and then kept constant at 25 C.° by an external heater/cooler. Electrophoresis was stopped when the tracking dye (bromphenol blue) reached the bottom of the 92 mm long gel, which happened in about two hours and 20 minutes. The sample (10 μl) included DNA molecules from the 1 kb ladder (BRL) with the following sizes: 12216, 11198, 10180, 9162, 8144, 7126, 6108, 5090, 4072, 3054, 2036, 1636, 1018, 516, 506, 396, 344, 298, 220, 201, 154, 134 and 75 base pairs. Under the electrophoretic conditions specified, the fragments larger that 4072 bp migrated as one broad band and 75 bp fragment migrated out of the gel. The gels were stained with ethidium bromide (about 0.2 μg/ml in water) overnight and then destained in water for at least two hours. A strip of the gel, 2–3 wide, was cut from the middle of the sample lane which was 5.5 mm wide. The cutting was done by a 0.17 mm thick nylon string (fishing line) after placing the gel on a cylindrical glass bottle. The strip was then released from the plastic support (Gel Bond, FMC) and placed on its side on a UV transilluminator box to visualize the DNA bands.

Example 1

A 6% poly(NAT) gel was polymerized in 30 mM TAE buffer and run in the same buffer as specified above. FIG. 2 represents a side view of DNA bands in the gel.

Example 2

A 6% poly(NAT) gel of the composition specified in Example 1 was polymerized between two Gel Bond sheets. The sheet on the top was shorter and extended from just after the sample wells to the gel end. The sample and electrophoretic conditions were as described in Example 1. At the end of the run, the plastic support from the top was removed with the nylon string and the gel was then stained. The DNA pattern in this gel is shown in FIG. 3. It was noted that the bands, although essentially vertical, were round and somewhat more diffuse than in the gel of FIG. 2.

Example 3

A 6% poly(NAT) gel was prepared in the same way as described in Example 1, except that the buffer was composed of 30 mM Tris, 11 mM acetate and 1.5 mM EDTA-free acid. Thus there was no sodium in the gel and in the running buffer. FIG. 4 shows the bending of DNA bands in this gel.

Example 4

A 6% poly(NAT) gel was prepared as described in Example 1, except that the monomer and cross-linker were dissolved in a buffer composed of 30 mM N-methyl glucamine and about 15 mM gluconic acid (the buffer contained in four liters 23 ml of the 50% gluconic acid water solution, technical grade, Fluka) pH 9.5. The gluconic acid solution had a brownish color. The gel was run in the Tris-acetate-EDTA-free acid buffer of Example 3. FIG. 5a shows DNA bending in the apparatus equipped with one electrode and FIG. 5b in the apparatus with two electrodes. In these gels DNA bands migrated further close to the bottom.

Example 5

A 6% poly(NAT) gel was prepared in the same way as described above, except that the monomer and cross-linker were dissolved in water. After polymerization the gel was soaked for 16 hours in 1 l of the 30 mM TAE buffer with gentle shaking. The ions left over, after polymerization diffused out of the gel and their concentration in the gel was expectedly reduced about 50 fold. The gel equilibrated with the TAE buffer was run in the same buffer under conditions outlined above and the DNA pattern from that gel is shown in FIG. 6. The bending is similar to that of FIG. 2.

Example 6

A 6% poly(NAT) gel was polymerized in water and equilibrated against 30 mM N-methyl glucamine, 15 mM gluconic acid buffer as described in Example 5. The gel was run in the same; N-methyl glucamine-gluconic acid buffer. FIG. 7 shows that the bending pattern resembles to that displayed in FIG. 5.

Example 7

A 6% poly(NAT) gel was polymerized in water and without any further treatment the gel was run in an electrophoresis buffer composed of TEMED and ammonium persulfate of the concentrations identical to those in the gel (15 mM TEMED and 1.65 mM ammonium persulfate). The electrophoresis buffer was prepared one day in advance to allow for decomposition of persulfate. FIG. 8 shows the DNA pattern in this gel. No DNA damage, possible by radicals derived from persulfate, was observed as smearing of the bands.

Example 8

A series of 6% poly(NAT) gels was polymerized with the same amounts of TEMED and sodium persulfate (15 mM TEMED and 1.65 mM sodium persulfate) but at various concentrations (12, 15, 18, 21, 24, 27 and 30 mM) of the TAE buffer. The best resolution seen on the photograph taken from above was at 18 mM TAE, and as shown in FIG. 9, DNA bands in that gel are essentially vertical.

Example 9

The electrical current at several voltages was measured in 300 ml of the TAE buffer at 18° C. In this apparatus the upper compartment was permanently separated from the lower compartment in order to reduce errors due to differences in the buffer volume. The electrodes were vertically distant 6 mm and 11 cm apart. The level of buffer was 34 mm above the upper electrode. The values for buffer are given in the first column of Table 1. The second column contains the values read on the power supply when three gels polymerized in 18 mM TAE buffer were placed in 349 ml of the buffer. The volume of buffer was reduced to compensate for the volume of three gels (51 ml). When three gels polymerized in 30 mM TAE buffer were placed in 349 ml of the buffer, the values in column three were measured.

TABLE 1

| Voltage (V) | Current (mA) | | |
|---|---|---|---|
| 10 | 16 | 16 | 16 |
| 20 | 35 | 35 | 38 |
| 40 | 77 | 76 | 79 |
| 60 | 117 | 117 | 122 |
| 80 | 158 | 159 | 164 |
| 100 | 200 | 199 | 208 |
| 120 | 242 | 242 | 252 |

Example 10

Figure 10B:
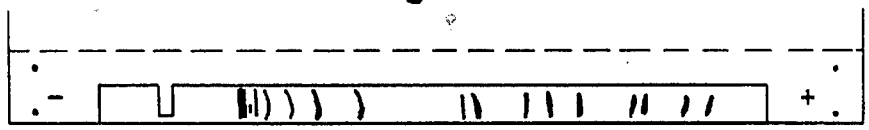

One 5 mm thick 6% poly(NAT) gel was polymerized in 18 and the other in 30 mM TAE buffer. As shown in FIGS. 10a and 10b, the bands representing 1 to 4 kbp fragments are more bent in the gel containing 18 mM than in the gel containing 30 mM TAE. The sample volume in these gels was 25 μl.

Example 11

A series of 9% poly(NAT) gels 3 mm thick was polymerized in the TAE buffer of different concentrations (18, 25, 30, 40, 50 and 60 mM). All gels were run in 30 mM TAE buffer at 7 V/cm for 4.5 h. From FIGS. 11a and 11b it can be seen that at 18 mM TAE the DNA bands are bent but at 50 mM they are essentially vertical. The bands are also more round and they migrate slightly closer to the bottom.

Example 12

A series of polyacrylamide gels containing 4.85 g of acrylamide and 0.150 g of Bis in 100 ml was polymerized with the same amounts of TEMED and sodium persulfate as described in Example 8, but at different concentrations (15, 20, 25, 30, 35 and 40 mM) of the TAE. All gels were run in 30 mM TAE at 7 V/cm for 2 hours and 10 min. The bending was present at all concentrations but it was more pronounced at 20 (FIG. 12a) than at 35 mM TAE (FIG. 12b).

Example 13

Four 4% hydroxyethyl-agarose gels (NuSieve, FMC) were cast in 30 mM TAE buffer. Than each gel was incubated separately in one liter of 30, 35, 40 or 45 mM TAE buffer for 16 hours. The gels were run in 30 mM TAE at 7 V/cm for 1 hour and 55 min. The sample volume was 25 μl. In the gel containing 30 mM TAE the DNA bands migrated slightly more near the bottom (FIG. 13a) but they were essentially vertical in the gel which contained 5 mM TAE (FIG. 13b). In this gel the bands were also more round.

Example 14

The electrical current at 80 V and 18° C. is given for different solutions containing ions present in the gels or buffers during electrophoresis (Table 2). The measurement was carried out in 300 ml of each solution as described in Example 9. The solutions containing sodium persulfate were prepared 24 h before measurement.

TABLE 2

| Solution | Current (mA) | |
|---|---|---|
| 5 mM sodium acetate | 64 | |
| 15 mM Tris-acetate | | 129 |
| 30 mM Tris-15 mM acetate | 130 | |
| 30 mM TAE | | 158 |
| 5 mM potassium acetate (KOAC) | | 80 |
| 10 mM potassium acetate | 153 | |
| 15 mM potassium acetate | 228 | |
| 5 mM sodium sulfate | 162 | |
| 5 mM sodium chloride | 88 | |
| 5 mM potassium chloride | 105 | |
| 2 mM $Na_2EDTA$ + 2 mM NaOH | | 79 |
| 18 mM TAE, 15 mM TEMED, 1.65 mM sodium persulfate | | 200 |
| 50 mM TAE, 15 mM TEMED, 1.65 mM sodium persulfate | | 346 |
| 15 mM TEMED, 13.5 mM acetate, pH 8.0 | 129 | |
| 14.3 mM TAE, 5.2 mM KOAc | 156 | |

Example 15

A 6% poly(NAT) gel was polymerized in a solution containing 15 mM TEMED, 1.65 mM sodium persulfate, 22.5 mM acetate and 11.6 mM potassium (pH 8.0). In this solution the current transported by anions and cations should be identical. Current was 370 mA at 80 V. The gel was run in the 26.6 mM TAE-9.7 mM KOAc buffer. The current at 80 V was 268 mA. The DNA pattern is shown in FIG. 14. The pH of this buffer was essentially equal before and after electrophoresis.

Example 16

A 9% poly(NAT) gel was polymerized in the same buffer as the 6% gel of Example 15, but the running buffer was 15.3 mM TAE-5.6 mM KOAc. The gel was run at 80 V for three hours and the DNA bands are shown in FIG. 15.

The foregoing invention has been described in considerable detail, and it will be apparent to those skilled in the art that modifications and changes may be made in the materials utilized, procedures and in the electrophoresis method without departing from the concept and scope of the invention as described in the following claims.

What we claim is:

1. In an improved elongated electrophoretic element, for separation of molecules, comprising:
   a water insoluble gel, and a gel buffer comprising ions within interstices of the gel;

said electrophoretic element being adapted to be immersed in an electrophoresis buffer comprising ions in contact with electrodes, where the separation of said molecules is achieved by differential migration of the molecules in said electrophoretic element in response to electric current passed between said electrodes;.

the improvement comprising:

said gel comprising at least 2% of polymer dry weight, said gel having composition or concentration of at least one of the ions in the interstices of the gel which is different form the composition or concentration of at least one of the ions in the electrophoresis buffer, and the composition and concentration of said ion in the gel interstices being adjusted in relation to the composition and concentration of said ion in the electrophoresis buffer in such a way that at the end of electrophoresis, the separated bands of molecules are substantially normal to the direction of migration of said molecules in said electrophoresis element.

2. An electrophoretic element of claim 1, wherein the gel comprises a polymer selected from synthetic or natural polymers.

3. An electrophoretic element of claim 2, comprising a poly(NAT) gel.

4. An electrophoretic element of claim 2, comprising a polyacrylamide gel.

5. An electrophoretic element of claim 2, comprising an agarose gel.

6. An electrophoretic element of claim 1, wherein the composition or concentration of ions in the gel is such that the same composition or concentration of ions in water has a higher conductivity than the conductivity of the electrophoresis buffer.

7. An electrophoretic element of claim 6, wherein the composition of ions in the gel is identical to that in the electrophoresis buffer but the concentration of ions is higher in the gel.

8. An electrophoretic element of claim 6, wherein the composition of ions in the gel differs from the composition of ions in the electrophoretic buffer.

9. An electrophoretic element of claim 6, wherein the gel comprises additional ions necessary for formation of the gel.

10. An electrophoretic element of claim 6, wherein the gel comprises additional ions as a byproduct of the gel formation.

11. An electrophoretic element of claim 6, wherein the gel comprises at least two anions and two cations at such a ratio that current is equally transported by anions and cations.

12. An electrophoretic element of claim 6, wherein the buffer comprises at least two anions and two cations at such a ratio that current is equally transported by anions and cations.

13. An electrophoretic element of claim 6, wherein the gel and buffer each comprise at least two anions and two cations at such a ratio that current is transported equally by anions and cations.

14. An electrophoretic element of claim 1, including means to adjust the ratio of current density and conductivity in the gel and electrophoresis buffer respectively in relation to the bending of said bands.

15. An-electrophoretic element of claim 14, wherein said means comprises varying the concentration of ions in the gel or in the buffer.

16. An electrophoretic element of claim 14, wherein said means comprises varying the composition of ions in the gel or in the buffer.

17. An electrophoretic element of claim 14, wherein said means comprises varying the composition and concentration of ions in the gel or in the buffer.

18. An electrophoretic element of claim 14, wherein said means comprises varying thickness or length of the gel.

19. An electrophoretic element of claim 14, wherein said means comprises varying concentration of the polymer comprising the gel.

20. An electrophoretic system comprising an elongated electrophoretic element as claimed in claim 1 wherein the ionic composition and concentration in said buffer is related to the ionic composition and concentration in the interstices of said gel such that the ratio of current density and conductivity (i/K) remains substantially constant in the gel cross-section through which a band migrates during electrophoresis.

21. An improved electrophoretic method comprising using at least one electrophoretic element of claim 1 as a medium for the separation of molecules.

22. An improved electrophoretic method comprising using the electrophoretic system of claim 20.

23. A method of forming a substantially water insoluble elongated gel element, suited to use in electrophoretic separation of molecules adapted to be passed through the long dimension of said elongated gel element, by having an effective amount of an electric current imposed across the long dimension of said element while it is effectively immersed in a conductive electrophoresis buffer comprising ions in an aqueous buffer medium;

said method comprising:

forming an elongated, substantially water insoluble gel, having interstices therein, comprising at least 2% polymer dry weight; and providing buffer ions in said interstices of a composition and/or concentration which is sufficiently different from the concentration and/or composition of ions in said electrophoresis buffer that, upon the imposition of said electric current across said element, said molecules differentially migrate through said element forming band normal to the direction of migration which are substantially normal to the direction of migration.

24. A method of claim 23, wherein said gel is formed by free-radical polymerization.

25. A method of claim 23, wherein the gel is fixed to a solid support.

26. A method of claim 23, including the further step of adjusting the composition and/or concentration of the buffer ions in the interstices of the gel as compared to the composition and/or concentration of the buffer ions in the electrophoresis buffer by:

observing the declination, from normal to the direction of migration, of separated bands corresponding to said molecules migrating in said medium; and then changing said relative composition and/or concentration of ions amount sufficient to cause said bands to become more normal to the direction of migration of said molecules.

27. A method of claim 26, wherein the composition and/or concentration of the buffer ions in the interstices of the gel as compared to the composition and/or concentration of the buffer ions in the electrophoresis buffer are adjusted by adding ions into a gel forming composition.

28. A method of claim 26, wherein the composition and/or concentration of the buffer ions in the interstices of the gel as compared to the composition and/or concentration of the buffer ions in the electrophoresis buffer are adjusted by equilibrating said gel in said gel buffer.

29. A method of claim 23, comprising varying the current density and conductivity in said elongated gel by varying the length of the gel element.

30. A method of claim 23, comprising varying the current density and conductivity in said elongated gel by varying the thickness of the gel element.

31. A method of claim 23, comprising varying the current density and conductivity in said elongated gel by varying the polymer concentration of the gel element.

32. An electrophoresis system, for causing molecules in a mixture of molecules fed thereto to migrate therein and, at the end of electrophoresis, to form bands which are indicative of the molecular weight of individual of said molecules, which system comprises:

container means;

a buffer solution, containing a multiplicity of ions in an aqueous medium, disposed within said container means;

substantially horizontally disposed, elongated gel element means having interstices therein substantially completely submerged in said buffer;

electrodes in effective contact with said buffer solution disposed proximate to each end of said gel element means;

means for imposing electric potential between said electrodes such that current flows through said system; and an ion concentration and/or composition in the interstices of said elongated gel which is sufficiently different from the ion concentration and/or composition in the buffer solution to cause said bands to be more normally disposed with respect to the direction of migration of said molecules than they would be if the composition and concentration of said ions was the same at the start of said electrophoresis.

* * * * *